(12) United States Patent
Reddy et al.

(10) Patent No.: US 6,858,430 B1
(45) Date of Patent: Feb. 22, 2005

(54) PROCESS FOR CULTIVATION OF ALGAE

(75) Inventors: Chennur Radhakrishna Reddy, Bhavnagar (IN); Om Prakash Mairh, Bhavnagar (IN); Guru Rajakrishna Kumar, Bhavnagar (IN); Kuruppan Eswaran, Bhavnagar (IN); Peddi Venkata Subba Rao, Bhavnagar (IN); Kalpana Harish Mody, Bhavnagar (IN); Pushpito Kumar Ghosh, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 16 days.

(21) Appl. No.: 09/656,561

(22) Filed: Sep. 7, 2000

(51) Int. Cl.[7] .............................. C12N 5/00; C12N 5/02
(52) U.S. Cl. ....................................................... 435/420
(58) Field of Search ......................................... 435/420

(56) References Cited

PUBLICATIONS

Dawes, C.J. et al., "Branch, Micropropagule and tissue culture of the red algae *Eucheuma denticulatum* and *Kappaphycus alvarezzi* farmed in the Philippines", Kluwer Academic Publishers, J. of Applied Phycology 3: 247–257, 1991.*

Mairh, O.P. etal., "Culture of marine red alga *Kappphycus striatum* (Schmitz) Doty on the Saurashtra region, west coast of India," Indian Journal of Marine Sciences, vol. 24, Mar. 1995, 24–31.*

Campbell, N.A. et al., "Biology," sixth edition, 2002, Benjamin Cummings, pp. 564 and 784.*

* cited by examiner

Primary Examiner—Bruce R. Campell
Assistant Examiner—S B. McCormick-Ewoldt
(74) Attorney, Agent, or Firm—Merchant & Gould P.C.

(57) ABSTRACT

The present invention provides a tissue culture method for cultivation of marine algae, said method comprising the steps of (i) establishing axenic viable algal material by sequential treatment thereof in sterile sea water supplemented with domestic liquid detergent, incubating the treated material, (ii) culturing the axenic explants on agarified medium for induction of callus; (iii) excising and subculturing the calli from the axenic explants on fresh agar plates to obtain differentiated densely pigmented oval or spherical shaped micro-propagules (iv) subculturing the pigmented calli in agarified medium to achieve enhanced somatic embryogenesis and micro-propagule formation in pigmented filamentous callus, (v) transferring the filamentous calli with somatic embryos for morphogenesis and development of young plantlets; and (vi) cultivating algal biomass on a large scale by growing the young plantlets in enclosed perforated polythene bags.

18 Claims, 8 Drawing Sheets

(8 of 8 Drawing Sheet(s) Filed in Color)

PROCESS FOR CULTIVATION OF ALGAE

FILED OF THE INVENTION

The present invention relates to an improved process for cultivation of marine algae. This invention pertains to the field of macrophytic multicellular marine algae (seaweeds) and more particularly to the mariculture of seaweeds.

BACKGROUND OF THE INVENTION

Seaweeds are considered as an important source of phycocolloids such as agar, carrageenan and alginate. Agar and carrageenan are structural polysaccharides present in the cell walls of certain red algae, while alginate is derived from certain brown algae. Seaweed phycocolloids are widely used in various industries as emulsifying agents, gelling agents, stabilizers, thickeners and suspension agents, and thus regarded as value-added products of seaweeds. Traditionally, phycocolloids are extracted from the raw materials harvested from natural resources. However, the increasing utilisation of seaweeds coupled with the unavailability of sufficient raw material in nature eventually led to successful development of different efficient cultivation techniques as well as domestication and selection of strains.

PRIOR ART REFERENCES

J. R. Waaland (*Proc. of the Intl. Seaweed Symp.* 9, 241–247, 1979) in his studies attempted to select fast growing strains in *Gigartina exasparata* by comparing the growth rate of wild plants collected from different populations in experimental tank cultures. Subsequently, many strains with superior potential for growth and phycocolloid yield have been selected from wild populations of *Chondrus crispus, Gracilaria tikvahiae, Gracilaria verucosa*, etc. (D. P Cheney et al., *Proc. of the Intl. Seaweed Symp.* 10, 559–567, 1981; J. H. Ryther et al., *Proc. of the Intl. Seaweed Symp.* 9, 1–16, 1979; I. Levy and M. Friedlander, *Botanica Marina*, 33, 339–345, 1990). The main drawback associated with these strains is lack of predictability of performance as the selection is based on a specific environmental condition and thus, optimal performance is intimately related to the culture conditions under which selection was performed. Moreover, such selection, even if successful, yield typically only incremental benefits.

G. C. Trono, (*Seaweed Cultvation and Marine Ranching*, M. Ohno and A. T. Critchley, (eds.), JICA Publication, Japan, 75–88, 1993) has described the taxonomy and cultivation of *Eucheuma* and *Kappophycus*, and stated that growers do make a crude selection under the field farm conditions by screening and selecting the best plants from the harvest and use such plants as a source material for replanting for the next crop. The main drawback of cultivating such strains is inconsistency in crop yield due to lack of adaptability to seasonal changes in farming conditions.

C. J Dawes and E. W. Koch (*J. Appl. Phycology*, 3, 247–257, 1991) and C. J. Dawes, G. C. Trono and A. O. Lluisma (*Hydrobiologia*, 260/261, 379–383, 1993) made attempts to develop suitable methods for maintenance and propagation of selected clones of different cultivated varieties of *Eucheuma* through micro-propagation and tissue culture. Their studies laid more emphasis on establishment of suitable laboratory culture techniques for clonal propagation of farmed *Eucheuma* using tiny vegetative fragments. The main drawback of such propagation using micro-cuttings is that the progeny will possess only parental features and does not have a pronounced advantage over the parental populations in expression of desired traits.

D. P. Cheney, Wang and Le Zhong in U.S. Pat. No. 5,585,544, 1996 demonstrated a method of causing somatic cell hybridization between *Eucheuma cottonii* and *E. spinosum* by growing somatic algal tissue from each of the two species in very close proximity, in a nutrient solution, and isolated hybrid somatic shoots with more desirable end product features. The main limitation of somatic cell hybridization in algae is that so far it has not been successful in introducing new traits in offspring except transferring some existing traits from either one of the parent.

Several articles have been published on commercial farming and processing of *Kappaphycus* and *Eucheuma* (J. R. Lim and H. Porse, *Proc. of the Intl. Seaweed Symp.* 10, 601–606, 1981; H. Adnan and H. Porse, *Hydrobiologia*, 151/152, 355–358, 1987; R. Azanza-Corrales and P. Sa-a, *Hydrobiologia*, 204/205, 521–525, 1990; G. P. B. Samonte, A. Q. Hurtado-Ponce and R. Caturao, *Aquaculture*, 110, 1–11, 1993). G. C. Trono (*Seaweed Cultivation and Marine Ranching*, M. Ohno and A. T. Critchley (eds.), JICA Publication, Japan, 75–88, 1993) has described two types of cultivation methods such as fixed off-bottom mono-line method and floating raft or long line method which are followed universally for cultivation of *Eucheuma*. In both the methods, selected *Eucheuma* apical cuttings (50–100 g) with profuse branches are tied to cultivation ropes at 25–30 cm intervals using soft plastic tying material (in Philippines known as tie-tie method) and allowed to grow to one kilogram or more before they are harvested. The crop is harvested after every 60–90 days duration depending on the growth rate. There are several limitations and drawbacks in common for both mono-line method and floating raft or long line method. They are, (i) the propagules/seed material are directly subjected to grazers which may eat away the entire material and thus, adversely affect the subsequent crop production, (ii) as the plantings are unprotected, there will be incidences of wash off material from cultivation ropes due to unfavourable sea conditions, (iii) epiphytes and settlement of foreign particles during unfavourable sea conditions may require cumbersome and time-consuming cleaning of the seaweed to ensure desired quality of the end product.

O. P. Mairh et al. (*Indian J. Marine Sciences*, 24, 24–31, 1995) successfully demonstrated the feasibility of bag cultivation of *Eucheuma striatum* on experimental scale in field conditions. However, the main drawback of this method is that this resulted in decrease in their daily growth rate as compared to those grown in open waters without polythene bags.

The present invention overcomes the deficiency of attenuated growth in the bag by developing a rapidly growing strain from the conventional seaweed through in vitro tissue culture techniques which exhibits more or less the same growth potential in the bag as the parent plant does in the open waters.

OBJECTS OF THE INVENTION

The main object of the present invention is to provide a method for cultivation of marine algae, more particularly *Eucheuma*.

Another object of the present invention is to develop a fast growing variant of marine algae especially *Eucheuma* through tissue culture.

Still another object of the present invention is to develop a method which would enable to produce a large number of propagules (seedling material) clonally for large scale farming of important seaweeds.

BRIEF DESCRIPTION OF THE ACCOMPANYING DRAWINGS

The patent or application file contains at least one drawing executed in color. Copies of this patent or patent application publication with color drawing(s) will be provided by the Office upon request and payment of the necessary fee.

In the figure(s) accompanying this specification;

DETAILED DESCRIPTION OF THE INVENTION

Figure 1:
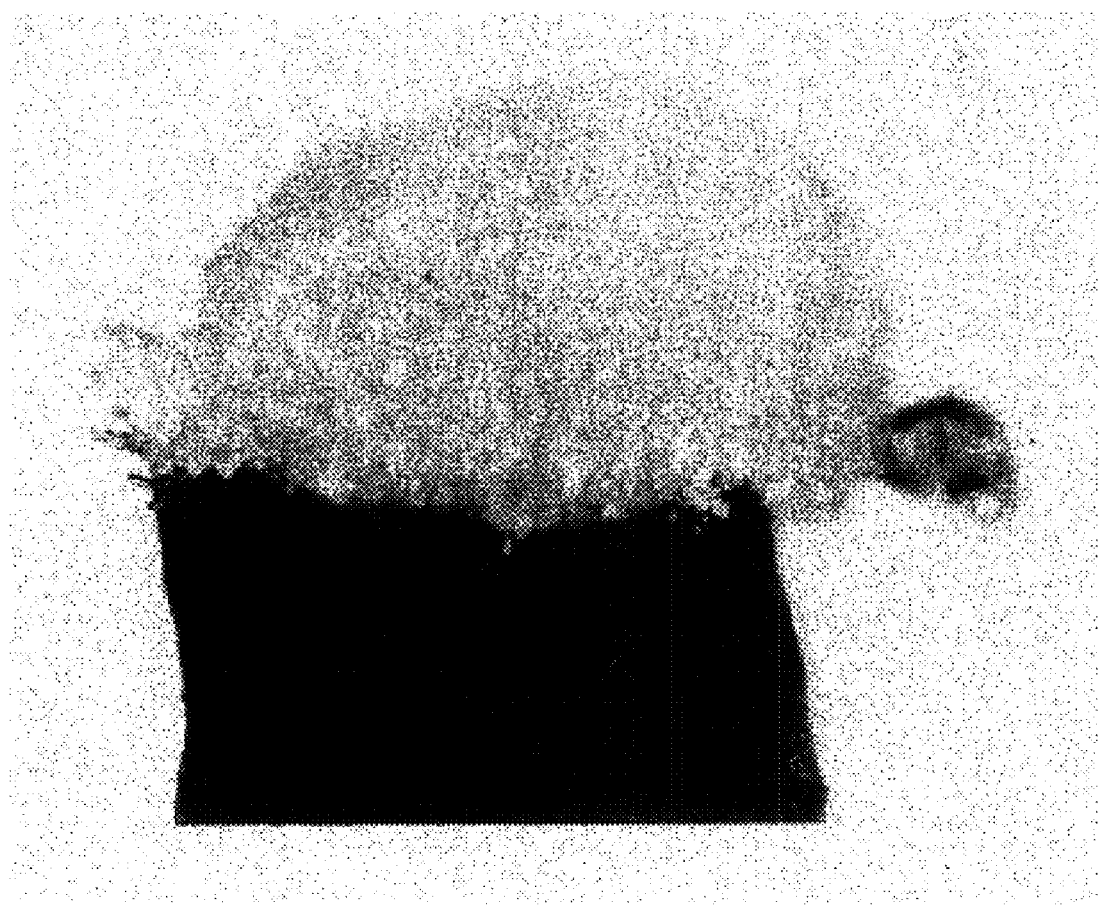
FIG. 1 represents the explant with callus of *Eucheuma* described in the invention.

Accordingly, the invention provides a tissue culture method for cultivation of marine algae, said method comprising the steps of:

a) establishing axenic viable material of algae for tissue culture by sequential treatment of the algal material in sterile sea water supplemented with domestic liquid detergent, povidine iodine and finally incubating the treated material in Provasoli enriched seawater (PES) medium with a broad spectrum antibiotic mixture and a fungicide for about 24 to 96 hours followed by thorough cleaning with sterile sea water to remove any traces of antibiotics and fungicide and blotting with sterile filter paper to obtain axenic explants;

b) culturing the axenic explants on agar plates fortified with PES medium at a temperature ranging between 20–25° C. in the presence of cool white fluorescent lights at about 20–50 $\mu$mol photons $m^{-2}s^{-1}$ irradiance and a 12:12 light and dark cycle for induction of callus;

c) excising the callus from the explant after a period of at least 40 days and subculturing the calli on fresh agar plates in the presence of cool white fluorescent lights with 40–60 $\mu$mol photon $m^{-2}s^{-1}$ irradiance and a 12:12 light and dark cycle to obtain differentiated densely pigmented oval or spherical shaped micro-propagules;

d) subculturing thin slices of the pigmented callus in agar plates in Provasoli Enriched Seawater (PES) medium containing plant growth regulators, for a period of about 20 to 40 days, in the presence of cool white fluorescent lights of 40–60 $\mu$mol photon $m^{-2}s^{-1}$ irradiance and a 12:12 light and dark cycle to achieve enhanced somatic embryogenesis and micro-propagule formation in pigmented filamentous callus;

e) transferring the filamentous calli with somatic embryos to liquid PES medium in agitated condition for morphogenesis and development of young plantlets with multiple shoots from propagules; and f) cultivating algal biomass on a large scale by growing the young plantlets in enclosed perforated polythene bags.

In an embodiment, the axenic explant is 1 to 6 mm long cuttings with 3–4 mm diameter from the upper part or distal part of the algal.

In another embodiment, the algal material is treated in PES medium with 1–5% antibiotic mixture comprising penicillin, streptomycin sulphate, kanamycin, nystatin and neomycin in 100 ml distilled water.

In still another embodiment, the axenic explants are cultured on agar plates containing 0.8–3% agar fortified with PES medium at 20–25° C. in the presence of 20–30 $\mu$mol photon $m^{-2}$ $s^{-1}$ cool white fluorescent light, irradiation with a 12:12 light and dark cycle.

In yet another embodiment, the calli is subcultured by growing thin slices of pigmented calli as embedded cultures in agar plates containing 0.3–0.6% agar and made in PES medium at 20–25° C. in the presence of cool white fluorescent light at 20–50 $\mu$mol photon $m^{-2}s^{-1}$, irradiation with 12:12 dark and light cycle to obtain profusely branched filamentous pigmented calli in each embedded block.

In an embodiment, the plant growth regulators are selected from 0.1–1.0 mg/l naphthalenacetic acid and 0.1 mg $l^{-1}$ each of naphthalenacetic acid and 6-benzylaminopurine.

In another embodiment, the axenic explants are cultured on agar plates for a period of about 40–45 days.

In still another embodiment, the apical cuttings are grown in polythene bags attached to long floating lines in the sea and harvested after a period of about 60 days.

In another embodiment, the young plantlets are cultured in perforated bags with annual seawater temperature ranging from 22.5° C.–28.5° C., pH from 7.81–8.26, salinity from 24.0‰–34.0‰, dissolved oxygen from 7.84 ml/l–15.68 ml/l, phosphate from 0.02 $\mu$mol–3.23 $\mu$mol, nitrate from 0.15 $\mu$mol–2.58 $\mu$mol and nitrite from 0.01 $\mu$mol–0.85$\mu$ mol.

In yet another embodiment, the micro-propagules are clonally propagated through somatic embryogenesis of pigmented filamentous callus.

In another embodiment, the young plantlets are grown in protective cultures in the sea for a period of at least 60 days in submerged transparent polyethylene bags with perforations, attached to floating long lines.

In still another embodiment, the process of formation of somatic embryos through somatic embryogenesis of pigmented callus is further enhanced by addition of plant growth regulators such as α-naphthalene acetic acid and 6-benzylaminopurine.

In another embodiment, the harvesting period of at least 60 days can yield a higher biomass or wherein the biomass yield can be maintained constant and the cultivation period reduced.

The present invention provides a method of an improved process for cultivation of algae which comprises a method of development of fast growing variant of farmed *Eucheuma* progeny through tissue culture which overcomes the deficiency of attenuated growth in the bag, wherein the axenic viable seaweed material for tissue culture is established by sequentially treating the selected plant material in 0.1–1% domestic liquid detergent (5–20 min), 0.1–2% povidine iodine (0.5% weight/volume available iodine) for 2–7 min and finally in PES medium with 1–5% antibiotic mixture (penicillin G–1 g, streptomycin sulphate–2 g, kanamycin–1 g, nystatin–25 mg and neomycin–200 mg in 100 ml distilled water) for 24–96 hours and axenic explants (1–6 mm long cuttings preferably from distal parts of the plant) of *Eucheuma* cultured on the agar plates (0.8–3% agar) fortified with PES medium at 20–25° C. under cool white fluorescent lights at 20–50 μmol photon $m^{-2}\ s^{-1}$ irradiance with a 12:12 light and dark cycle showed induction of callus which on subculture without explant provided darkly pigmented oval or spherical shaped micro-propagules, whose production is further enhanced by growing thin slices of pigmented callus (2 mm×3 mm×2 mm) as embedded cultures in 3 mm thick agar plates (0.3–0.6% agar) made in PES medium, however, addition of plant growth regulators particularly 0.1–1.0 mg $1^{-1}$ of naphthalenacetic acid or 0.1 mg $1^{-1}$ each of naphthalenacetic acid and 6-benzylaminopurine to agar medium further enhanced the process of formation of somatic embryogenesis and micro-propagule production in pigmented filamentous callus, and transfer of such callus mass with somatic embryos to the liquid PES medium in agitated condition facilitated morphogenesis and development of young plantlets from propagules, which are in field cultivation exhibited superior growth with greater than two-fold increase in biomass over the control parent plant without compromising on the yield and quality of carrageenan derived from the seaweed, and also demonstrates a modified floating long line cultivation method wherein *Eucheuma* apical cuttings (preferably with branches) of 100 g fresh weight are grown inside a closed transparent polythene bag (450 guage; 60 cm×45 cm) with perforations of 4 mm diameter holes in 3 rows (each with 12 numbers of holes equidistantly placed) at 14 cm intervals on both sides, in the sea yielded a biomass of 1590±37.4 g. fresh weight (4.6% daily growth rate) for tissue culture progeny and 846.66±37.9 g. fresh weight (3.5% daily growth rate) for control parent plant in 60 days growth period.

In an embodiment, the methodology for preparing axenic viable plant material for tissue culture is established by sequentially treating the selected plant material in 0.1–1% domestic liquid detergent (5–20 min), 0.1–2% povidine iodine (0.5% weight/volume available iodine) for 2–7 min and finally in PES medium with 1–5% antibiotic mixture (penicillin G–1 g, streptomycin sulphate–2 g, kanamycin–1 g, nystatin–25 mg and neomycin–200 mg in 100 ml distilled water) for 24–96 h. The axenity of the material as treated above is confirmed by transferring onto Zobell 2216E agar plates for two weeks at 22–23° C. in an incubator.

In another embodiment, development of fast growing variants of farmed *Eucheuma* through tissue culture. Callus induction has been found viable in axenic explants grown aseptically on agar plates (0.8–3.0% agar) fortified with Provasoli enriched seawater (PES) medium at 20–25° C. under cool white fluorescent lights at 20–50 μmol photon $m^{-2}s^{-1}$ irradiance with a 12:12 light and dark cycle. After 40 days, the proliferated callus is excised from the explant and subcultured separately on fresh agar medium as above. Some of the subcultured calli on an agar plates, after 40 days growth, differentiated and produced densely pigmented spherical or oval shaped micropropagules (2–5 mm in diameter) which on transfer to liquid PES medium developed into young plantlets of *Eucheuma*. The repeated testing of many cloned plants in the field cultivation consistently showed that a sizable fraction (>90%) of the plants not only survive but also exhibit enhanced growth over the control parent plants.

In yet another embodiment, in vitro clonal production and propagation of micro-propagules through somatic embryogenesis of pigmented calli cells is demonstrated. For enhancing the production of micro-propagules, the subcultured pigmented calli is cut into several thin blocks (2 mm×3 mm×2 mm) and grown as embedded cultures inside the agar plates (0.3–0.6%) at 20–25° C. under cool white fluorescent lights at 20–50 μmol photon $m^{-2}s^{-1}$ irradiance with a 12:12 light and dark cycle. From each embedded block, profuse growth of branched filamentous pigmented callus is seen in first three weeks duration and thereafter regeneration of densely pigmented micro-colonies similar to somatic embryos in dark brown colour on branches of some filaments is observed. Transfer of such filamentous callus with somatic embryos to liquid enriched seawater medium (PES) facilitated rapid growth and morphogenesis in micro-propagules.

In still another embodiment, the process of formation of somatic embryos in pigmented filamentous callus is further enhanced by addition of plant growth regulators particularly 0.1–1.0 mg $1^{-1}$ of naphthalenacetic acid or 0.1 mg $1^{-1}$ each of naphthalenacetic acid and 6-benzylaminopurine to an agar medium.

In still another embodiment,the initial plantings, preferably apical cuttings with profuse branches, of about 100 g fresh weight are enclosed in perforated transparent polythene bags (450 gauge; 60 cm×45 cm) and grown by attaching the bags to floating long lines in the sea. The cuttings are grown as above in protective bags round the year and the crop was harvested at every 60–75 days period. The cuttings are grown to a biomass of 394.6±20.8 g. fresh weight (4.7% daily growth rate) in 30 days, 846.66±37.9 g. fresh weight (3.5% daily growth rate) over a period of 60 days cultivation.

In still another embodiment, a comparative yield potential of fast growing strains developed in the present invention and control parent plant in the field conditions is carried out by following the bag cultivation method. The fast growing variant yielded a fresh biomass of 1590±37 g. (4.6% daily growth rate) whereas the control parent plant yielded 846±38 g. (3.6% daily growth rate) as against 1726 g. (4.7% daily growth rate) obtained for open waters ones in 60 days cultivation period.

Inventive techniques are described below in detail for an improved process for cultivation of algae including development of a fast growing variant from tissue culture, mass production and propagation of micropropagules (seed stock) through somatic embryogenesis and a modified cultivation method for growing marine macroalgae. The desired algal organism should be photosynthetic and tolerant to various marine habitat conditions. Algae suitable for use with the invention are non-filamentous and anatomically complex thallophytic red (Rhodophyta) and brown (Phaeophyta) marine algae which have cartilaginous thallus with erect or prostrate habit and consist of cylindrical or compressed branches and form large biomass. Suitable algae may be chosen from the red algae preferably from the order of Gigartinales. Within the order of Gigartinales preferred genera are the genus of *Eucheuma*, e.g., *E. striatum, E. cotionii, E. denticulatum, E. spinosum, E. alvarezii* and *E. procrusteanum*; the genus of *Gigartina*, e.g., *G. intermedia, G. exasparata*; and the genus of *Chondrus*, e.g., *C. crispus*. Suitable genera of Phaeophyta are *Laminaria, Undaria, Ecklonia, Eisenia, Macrocystis, Sargassum* and *Turbinaria*. For obtaining axenic material, selected plant material is sequentially treated in autoclaved filtered seawater (sterilised seawater) with 0.1–1% domestic liquid detergent (5–20 min), 0.1–2% povidine iodine (0.5% weight/volume available iodine) for 2–7 min and finally in PES medium with 1–5% antibiotic mixture (penicillin G–1 g, streptomycin sulphate–2 g, kanamycin–1 g, nystatin–25 mg and neomycin–200 mg in 100 ml distilled water) for 24–96 h at 20–25° C. under cool-white fluorescent lamps at 25–30 $\mu$mol photon m$^{-2}$s$^{-1}$ irradiance with a 12:12 light:dark cycle. However, the plant material treated with 0.1% liquid detergent, followed by 1% povidine iodine and 3% of broad-spectrum antibiotics for two days become contaminant free and did not show any bacterial growth on Zobell medium even after three weeks of culture.

After establishing the procedure for obtaining axenic material, the explants (5 mm long cuttings preferably from distal parts of the plant) of *Eucheuma* cultured aseptically on an agar plates (0.8–3% agar) fortified with PES medium for about a month at 20–25° C. under cool white fluorescent lights at 20–50 $\mu$mol photon m$^{-2}$s$^{-1}$ irradiance with a 12:12 light and dark cycle. The callus induction was observed during first two weeks of culture. After 40 days, the proliferated filamentous branched callus excised from the explants and subcultured separately on fresh agar plates under similar conditions, except light which was increased to 50 $\mu$mol photon m$^{-2}$s$^{-1}$ irradiance, to induce morphogenesis and differentiation in callus. Some of the subcultured calli after about 40–50 days culture on agar plates did undergo morphogenesis and produced densely pigmented spherical or oval shaped micropropagules (2–5 mm in diameter) which on transfer to liquid PES medium developed into young plantlets of *Eucheuma*. The field viability and growth performance of these plants was tested repeatedly by transferring to experimental field cultivation site at Thoniturai (Gulf of Mannar, India). All the plants tested as above in the field consistently showed low mortality, with several of the plants exhibiting more than two-fold increase in fresh weight over control parent plants, over the same duration of cultivation. This trend has continued with negligible variation even for the third generation seaweed.

The production of micro-propagules clonally through somatic embryogenesis of pigmented callus has been established. The somatic embryogenesis and micro-propagule production may further be enhanced by subculturing thin section of pigmented filamentous callus blocks (2 mm×3 mm×2 mm) in 3 mm thick agar plates (0.3–0.6% agar) with PES medium as embedded cultures. The callus blocks implanted in an agar medium grew rapidly in one month and formed colored spots in an agar with abundantly growing branched filamentous pigmented callus. The newly regenerated filamentous callus from blocks eventually transformed to produce densely pigmented (dark brown colour) micro-colonies similar to somatic embryos in branches of some filaments. Addition of plant growth regulators particularly 0.1–1 mg l$^{-1}$ of naphthalenacetic acid or 0.1 mg l$^{-1}$ each of naphthalenacetic acid and 6-benzylaminopurine to an agar medium further enhanced the formation of somatic embryogenesis. Transfer of such filamentous callus with somatic embryos from solid (agar plates) medium to liquid PES medium facilitated rapid growth and morphogenesis in micro-propagules.

In the present invention, the selected *Eucheuma* cuttings, preferably with branches, as seed material, are grown completely in closed protective bags, more preferably transparent ones with perforations (4 mm diameter), which allow light penetration and seawater circulation needed for their sustainable growth while at the same time excluding the possibility of being grazed and settlement of foreign particles. The surface of the bags, on which however foreign matter settles, were cleaned weekly or whenever it is required. During the cultivation period, the annual seawater temperature ranged from 22.5° C.–28.5° C., pH from 7.81–8.26, salinity from 24.0‰–34.0‰, dissolved oxygen from 7.84 ml/l–15.68 ml/l, phosphate from 0.02 $\mu$mol–3.23 $\mu$mol, nitrate from 0.15 $\mu$mol–2.58 $\mu$mol and nitrite from 0.01 $\mu$mol–0.85 $\mu$mol in farm site. A yield of 1590±37.4 g. fresh weight was harvested after 60 days period from tissue culture raised plants, 846.6±37.9 g. fresh weight from control parent plant starting with initial seed material of 100 g. fresh weight.

The present invention reveals for the first time development of fast growing strains under in vitro conditions as well as a method of producing micro-propagules clonally on large scale through somatic embryogenesis of pigmented callus of anatomically complex thallophytic red alga. The earlier studies on tissue culture of seaweeds demonstrated the regeneration of entire plants de novo by transferring the callus to liquid medium. But in the present invention for the first time succeeded in producing somatic embryos like pigmented micro-colonies consisting of cells from as little as three to several hundred on agar plate itself. We found that the pigmented micro-colonies on agar plates under dim light conditions can ideally be preserved live for extended periods till needed. The daily growth of field grown plants raised from tissue culture have, in several cases, exhibited more than 40% increase over the control plants under similar conditions, At the end of 60 days, this translates to a two-fold increase in biomass over control which is more or less similar to that obtained for open waters. The semi-refined carrageenan yield from dry tissue culture raised plants is 43% and gel strength is 540 g. cm$^{-2}$ while for the control parent plant s the yield is 43% and gel strength of the carrageenan is 550 g. cm$^{-2}$. The inventive steps adopted in the present invention are (i) development of a methodology for obtaining a clean and axenic plant material for tissue culture, (ii) development of fast growing variants, with two-fold increase in growth without change in carrageenan yield and quality, through micro-propagules of pigmented callus, (iii) in vitro clonal propagation of micro-propagules through somatic embryogenesis of pigmented callus by growing as embedded cultures inside the agar plates, (iv) stimulation of process of formation of somatic embryos in pigmented callus using plant growth regulators such as naphthalenacetic acid and 6-benzylaminopurine and (v) cultivation of algae in an enclosed transparent plastic bags with perforations, which prevents grazing and provides pure raw material, free of contaminants likely to affect adversely the final processed product.

The following examples are given by way of illustration and therefore should not be construed to limit the scope of the present invention.

More specifically, the improved cultivation process includes the methodology for development of a clone with an improved trait, i.e., faster growth, through tissue culture and cultivation by long line floating method using a transparent polythene bag with small perforations, which prevents grazing and provides pure raw material, free of contaminants which are likely to affect adversely the final processed product kappa carrageenan (κ-carrageenan).

The main usage(s)/utility of the improved cultivation method includes the following: (i) methodology for development of soma clones with an improved trait, i.e., faster growth, through tissue culture, (ii) in vitro clonal propagation of seaweeds through somatic embryogenesis of callus cells, (iii) production and supply of uniform seed stock (micropropagules) on large scale through in vitro somatic embryogenesis of callus culture for practical farming of seaweeds, (iv) exploitation of the callus as a source for long term storage of germplasm, and (v) cultivation in a transparent polythene bag with small perforations, which prevents grazing and provides pure raw material, free of contaminants detrimental to the processed product, κ-carrageenan.

EXAMPLE 1

Preparation of Axenic Explants

To develop an axenic, viable and unialgal material for tissue culture, selective fragments (just below the apical portions with 4–5 mm diameter stem) of about 5 cm length were chosen from the thallus of *Euchema striatum* (=*Kappaphycus alvarezii*) collected from the cultivation farm. Prior to initiation of experiments, the plants were acclimatized to laboratory conditions by growing in PES enriched seawater medium in aerated flasks under coolwhite fluorescent lamps at 20 $\mu$mol photon m$^{-2}$s$^{-1}$ irradiance with a 12:12 light:dark cycle for ten days. During the acclimatization period the media in the flasks was replenished twice at five day period. After acclimatization, first, the fragments were extensively cleaned with a brush under microscope in an autoclaved filtered seawater (sterilised seawater) to remove any surface contaminants and subsequently treated in sequence in sterilised seawater with 0.1% domestic liquid detergent for 10 min, 1% povidine iodine (available iodine 0.5% w/v) for 2 min and finally incubated in PES medium supplemented with 3% of filter sterilised broad-spectrum antibiotic mixture (penicillin G-1 g, streptomycin sulphate-2 g, kanamycin-1 g, nystatin-25 mg and neomycin-200 mg in 100 ml distilled water) for 48 hours at 23° C. under cool-white fluorescent lamps at 25 $\mu$mol photon m$^{-2}$s$^{-1}$ irradiance with a 12:12 light:dark cycle. At each step, prior to proceeding to successive treatment, the algal pieces were rinsed with sterilised seawater to avoid cross contamination of chemicals. All the above operations, except the incubation of material in antibiotics, were performed on a Bioclean bench. The plant materials as treated above become contaminant free and did not show any microbial growth on Zobell agar plate even after two weeks of period.

EXAMPLE 2

Callus Induction in Axenic Explants

Figure 2:
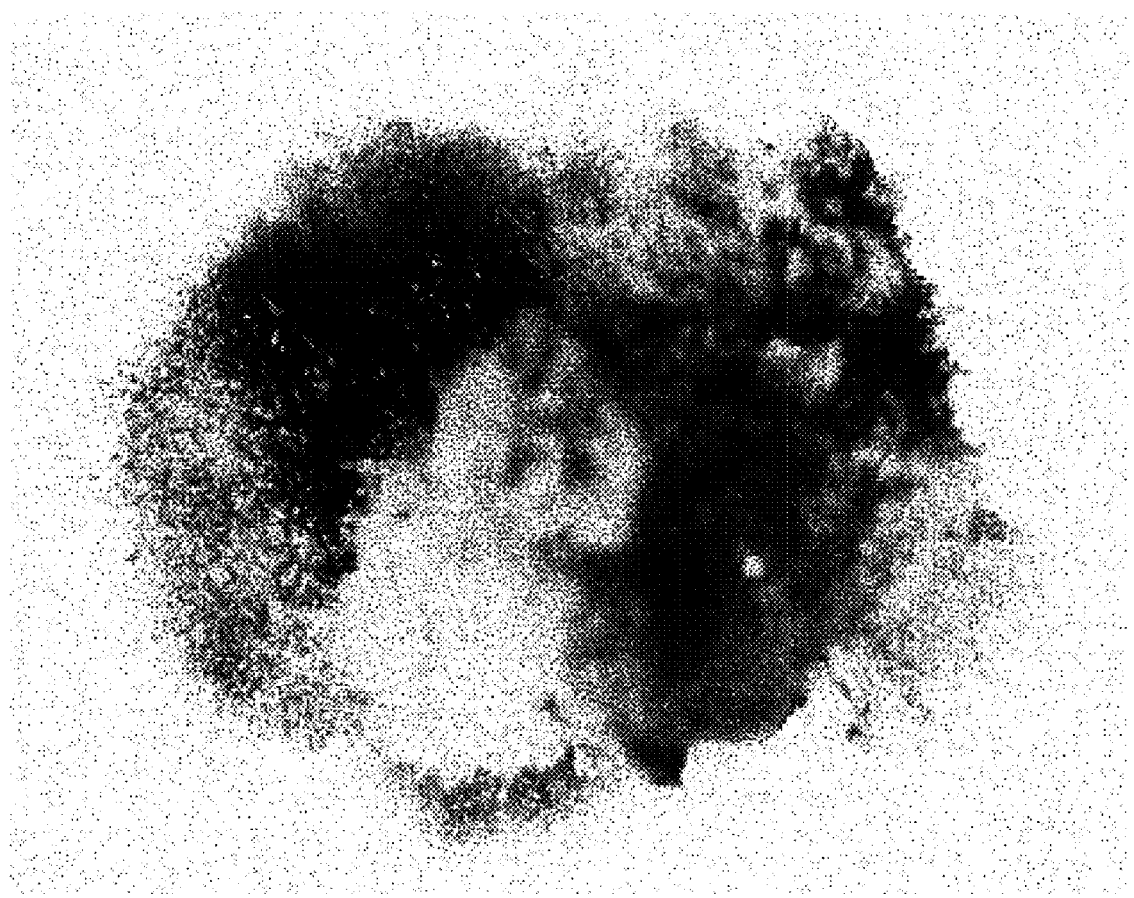
FIG. 2 represents profuse growth of subcultured *Eucheuma* callus excised from the explant.
Figure 3:
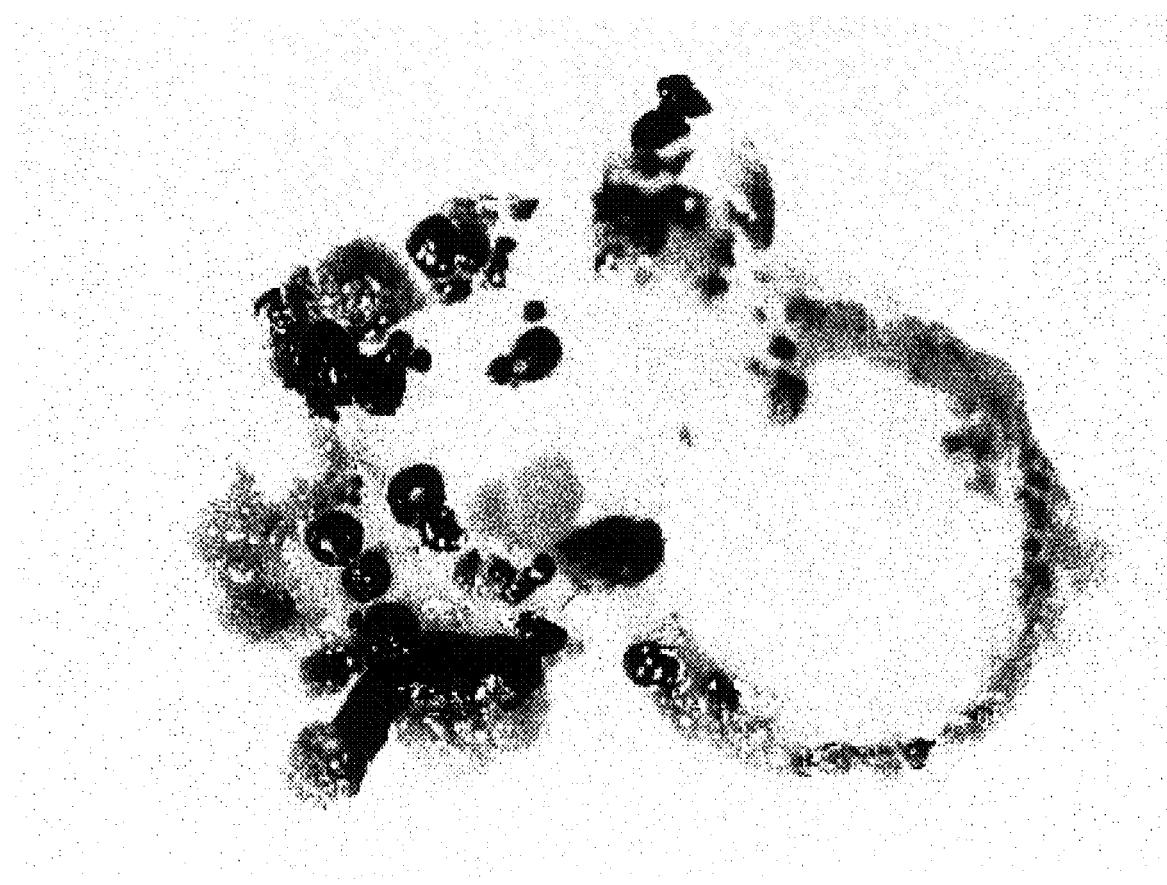
FIG. 3 shows spherical or oval shaped tiny micro-propagules on excised callus
Figure 4:
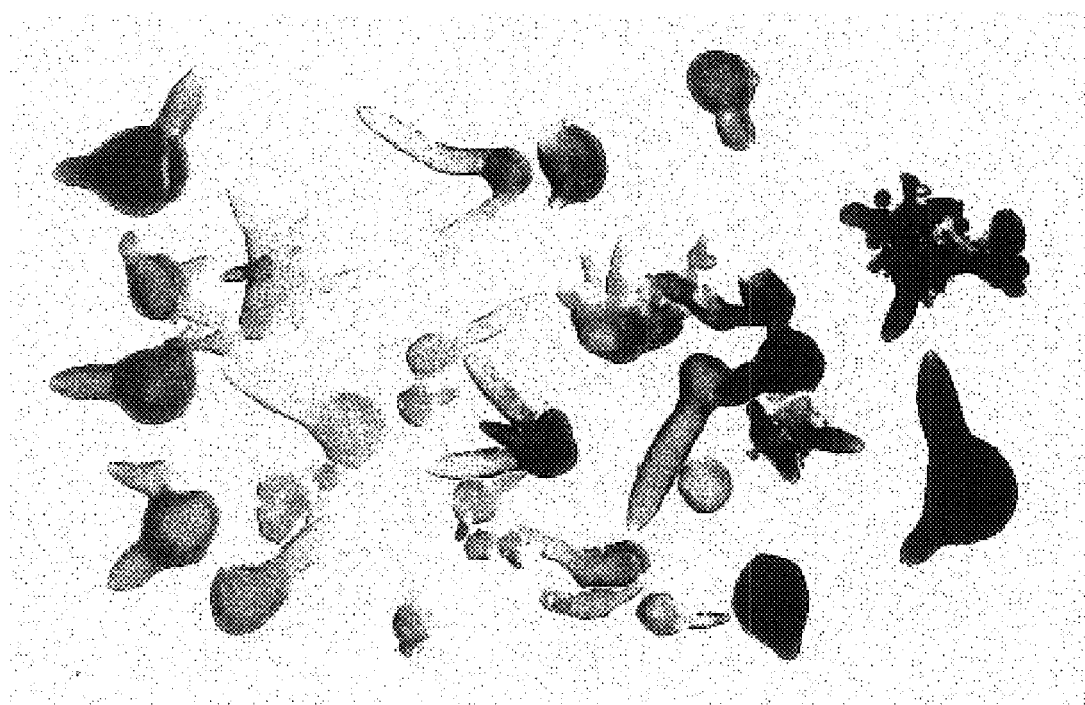
FIG. 4 represents the young propagules developed from tiny micro-propagules as described in one of the embodiments of the method of invention for development of fast growing strains.
Figure 5:
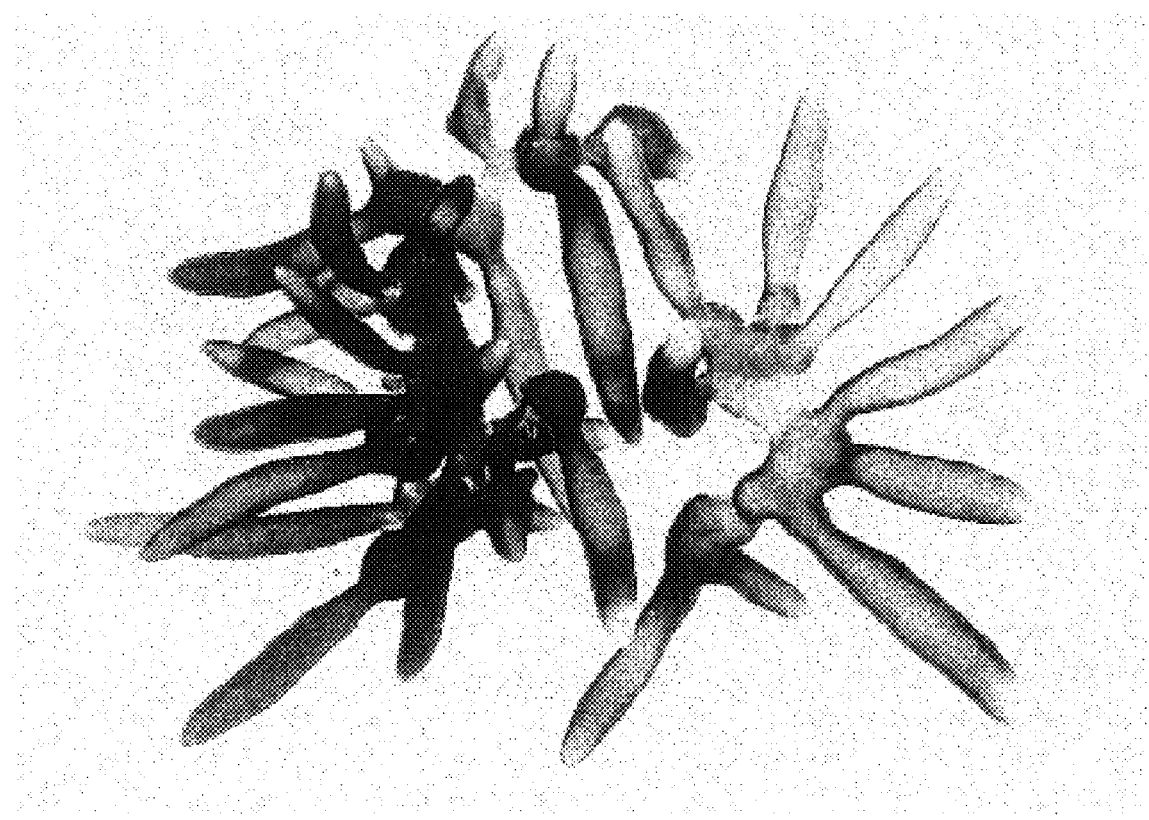
FIG. 5 represents the multi-branched young plantlets of *Eucheuma* regenerated from propagules.

Callus induction was carried out in axenic materials obtained by following the method described in Example 1. First, the plant material to be used for callus induction was thoroughly cleaned with sterilised seawater to remove any traces of antibiotics, and cut into 5 mm length explants and blotted with sterile filter papers to remove moisture as well as mucilage that exude from the cut ends which might some times become a source of microbial contamination even after a month of explant culture. All the explants were grown on 1.5% agar plates prepared with PES medium for about a month at 23° C. under cool white fluorescent lights at 25 $\mu$mol photon m$^{-2}$s$^{-1}$ irradiance with a 12:12 light and dark cycle. The callus induction was observed during the first two weeks of culture. After 50 days, the proliferated filamentous branched callus (FIG. 1) was excised from the plants and subcultured separately on fresh agar plates under similar conditions, except light which was increased to 50 $\mu$mol photon m$^{-2}$s$^{-1}$ irradiance, to enhance the growth of callus. Some of the subcultured calli (FIG. 2) after 50 days of culture on agar plates did undergo morphogenesis and produced densely pigmented spherical or oval shaped micropropagules (FIG. 3) of 2–5 mm diameter all over the callus. Further, culture of these propagules separately in liquid PES medium in agitation conditions grew into young propagules (FIG. 4) which eventually developed into young plantlets with multiple shoots (FIG. 5) within 3 weeks duration.

EXAMPLE 3

Somatic Embryogenesis and Clonal Propagation

Figure 6:
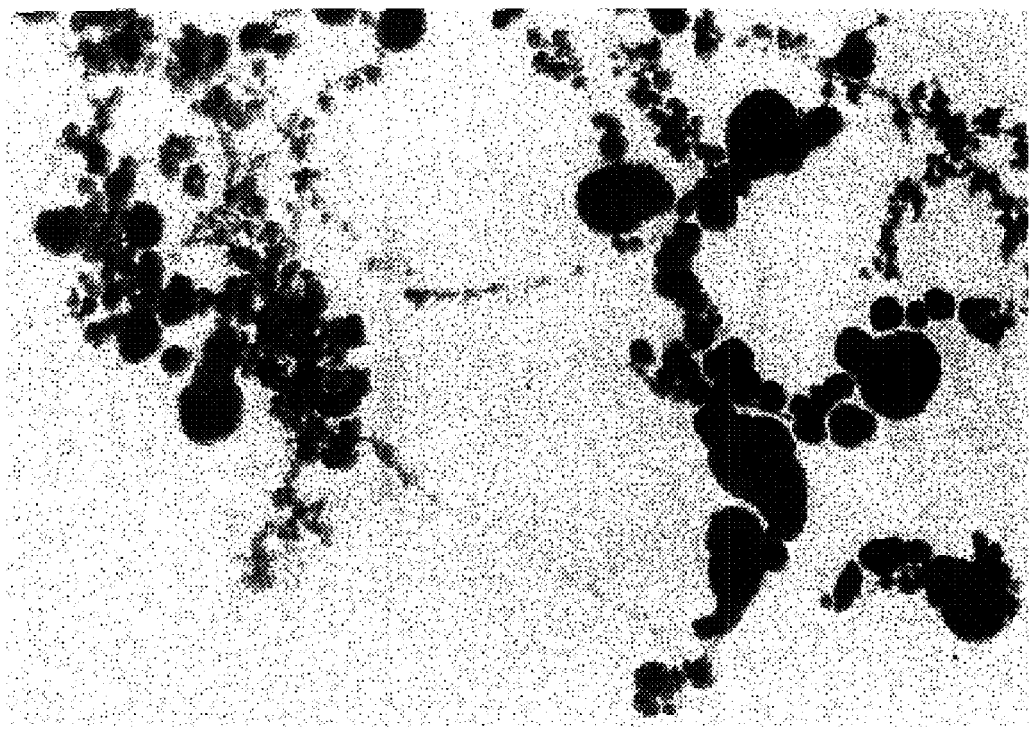
FIG. 6 represents in vitro development of somatic embryos from callus described in one of the embodiments of the method of invention for development of mass production of seed stock.

The production of micro-propagules clonally through somatic embryogenesis of pigmented callus of *Eucheuma* has been carried out. The somatic embryogenesis and micropropagule production may be enhanced by subculturing thin section of pigmented filamentous callus blocks (2 mm×3 mm×2 mm) in 3 mm thick agar plates (0.4% agar) with PES medium as embedded cultures at 23° C. under cool white fluorescent fights at 50 $\mu$mol photon m$^{-2}$s$^{-1}$ irradiance with a 12:12 light and dark cycle. The callus blocks implanted in an agar medium grew rapidly in one month and formed colored spots in an agar with abundantly growing branched pigmented filamentous callus. The newly regenerated filamentous callus from blocks eventually transformed to produce densely pigmented (dark brown colour) micro-colonies similar to somatic embryos (FIG. 6) on branches of some pigmented filamentous callus.

EXAMPLE 4

Enhancement of Somatic Embryogenesis by Plant Growth Regulators

The process of production of micro-propagules in pigmented filamentous callus of *Eucheuma* was further enhanced by supplementing the growth medium with plant growth regulators such as naphthalenacetic acid (auxin) and 6-benzylaminopurine (cytokinin). Thin slices of pigmented callus blocks (2 mm×3 mm×2 mm) were grown as embedded cultures in 3 mm thick agar plates (0.4% agar) made in of PES medium supplemented with 0.1, 1.0 mg l$^{-1}$ of naphthalenacetic acid, or with 0.1 mg l$^{-1}$ each of naphthalenacetic acid and 6-benzylaminopurine. All the Petri dishes with embedded callus were maintained at 23° C. under cool white fluorescent lights at 50 $\mu$mol photon m$^{-2}$s$^{-1}$ irradiance with a 12:12 light and dark cycle. The callus blocks implanted in an agar medium grew rapidly in one month and formed dense pigmented micro-colonies similar to somatic embryos in an agar medium. Transfer of such pigmented callus mass from solid (agar plates) medium to liquid PES medium facilitated rapid growth and morphogenesis in micro-propagules. For achieving the rapid morphogenesis of micro-propagules, agitated culture was preferred.

EXAMPLE 5

Cultivation of *Euceuma* by Floating Long Line Method

At the beginning, the yield data of cultivated *Eucheuma* by traditional floating long line method in open waters was established. In this method, selected *Eucheuma* cuttings, preferably apical ones with profuse branching, of about 100 g fresh weight, as initial seed material for planting, were tied in ten replicates directly at 30 cm intervals to a polypropylene rope (8 mm diameter and 30 meter length) which hung between two bamboo poles (about 5 m length) fixed at the bottom. The bamboo poles are arranged in rows at 1 m intervals with the same distance to form plots. The distance of rope from the ground is about 0.5 meter during low tide and 1.0–1.5 meter during high tide. The growth of plants was determined by weighing the individual fresh plants at 30 days interval and daily growth rate was calculated using the formula: $r=(W_t/W_o)^{1/t}-1\times100$, where r stands for daily growth rate in percent, $W_t$ is the wet weight at day t, $W_o$ is the initial wet weight. The mean biomass and daily growth rate, over 30 days were 450 g. fresh weight and 7.3% respectively, and for 60 days were 1726 g. fresh weight and 4.7% respectively for plants grown in open waters.

Figure 7:
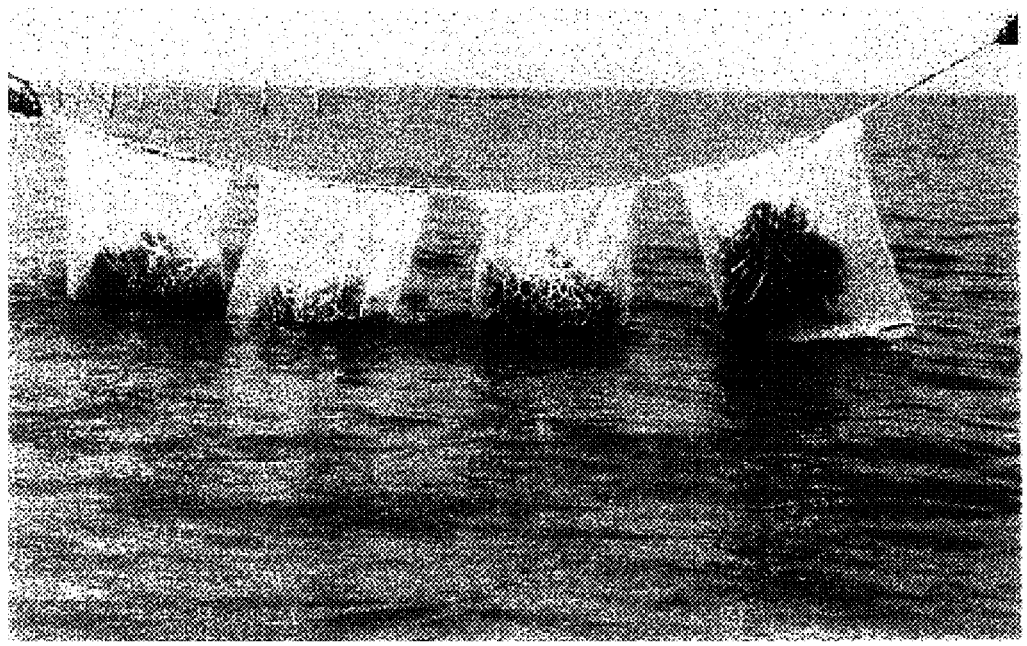
FIG. 7 represents the floating long-line cultivation system of *Eucheuma* in polyethylene bags used in one of the embodiments of the method of improved process for cultivation.

EXAMPLE 6
Cultivation of *Eucheuma* in Polythene Bags by Floating Long Line Method In this method, selected *Eucheuma* cuttings, preferably apical ones with profuse branching, of about 100 g fresh weight as initial seed material for planting were grown inside closed transparent polythene bags (450 guage; 60 cm×45 cm) with perforations (for sea water circulation) in ten replicates till harvest. Leaving 18 cm from the open end of the bag, perforations were made on both the sides, with 4 mm diameter holes in 3 rows (each with 12 numbers of holes equidistantly placed) at 14 cm intervals. Thus each bag consisted of 72 holes taking both sides together (i.e., 36 holes on one side). The bags were sewn with nylon thread and attached to the floating rope (FIG. 7). In total fifty bags at about 10 cm intervals are tied to one rope as above. The crop was harvested after 60 days and weighed for calculating the growth rate by using formula described in Example 5.

Figure 8:
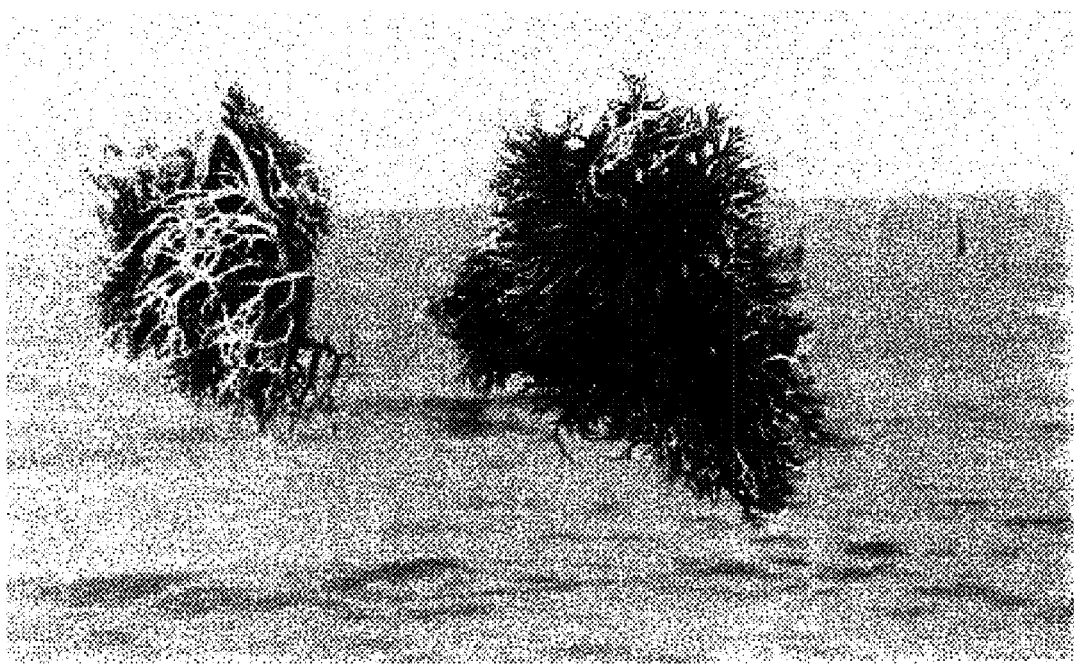
FIG. 8 shows the comparative growth of the control parent plant and the tissue culture plant derived therefrom.

EXAMPLE 7
Comparative Study of Growth, Carrageenan Yield and Gel Properties of Tissue Culture Progeny and Control Plants A comparative study on growth (FIG. 8), carrageenan (semi-refined) yield on dry seaweed weight basis, and carrageenan gel strength of field grown plants raised from tissue culture progeny and control parent plants was carried out. Both type of plants were grown in 10 replicates in closed transparent polythene bags by floating long line method as described earlier in Example 6. An average biomass of 394.58±20.8 g. fresh weight (4.7% daily growth rate) was obtained for 30 days and 846.6±38 g. fresh weight (3.5% daily growth rate) for 60 days, while tissue culture plants had 711.6±13 g. fresh weight (6.8% daily growth rate) for 30 days and 1590±37 g. fresh weight 4.6% daily growth rate) for 60 days period. Semi-refined carrageenan content was obtained by first cooking the 10 g of pre-cleaned seaweed in 200 ml of 8% KOH solution for 1.5 h, decanting the filtrate, neutralizing the residual material, and washed with distilled water. Following the washing in water, the material is dried thoroughly at 40° C. and weighted to estimate yield. Gel strength was measured with gel strength tester (Nikkansui, Co. Japan) by preparing a gel of 1% carrageenan by boiling in 1% KCl solution. The yield for the control parent plant as also for the plants grown from mocropropagules were comparable at 43% on dry seaweed basis. The corresponding gel strengths were 550 gcm$^{-2}$ and 540 gcm$^{-2}$, respectively.

ADVANTAGES

The main advantages of the present invention are:
1. A new method of improving a parent plant to introduce improved traits such as fast growth.
2. A method of producing large number of micro-propagules (seed material) rapidly from desired strains.
3. A means of storage of germplasm in viable form, i.e., as somatic embryos, on agar plates.
4. An improved method of cultivation of seaweeds which reduces adverse impact of the vagaries of nature such as strong water current and damage to crops by grazers and epiphytes and yet allows the same or better growth rate than what is realised with the parent plant in open waters.
5. An improved method of cultivation which provides material of highest purity free from all contaminants detrimental to the quality of final processed end product.

What is claimed is:
1. A in vitro clonal propagating method for cultivation of marine algae, said method comprising the steps of:
   a) establishing axenic viable material of algae for tissue culture by sequential treatment of the algal material in sterile sea water with domestic liquid detergent, and povidine iodine and incubating the treated material in Provasoli enriched seawater (PES) medium with a broad spectrum antibiotic mixture and a fungicide for about 24 to 96 hours followed by thorough cleaning with sterile sea water to remove any traces of antibiotics and fungicide and blotting with sterile filter paper to obtain axenic explants;
   b) culturing the axenic explants on agar plates fortified with PES medium at a temperature ranging between 20–25° C. in the presence of cool white fluorescent lights at about 20–50 μmol photon m$^{-2}$s$^{-1}$ irradiance and a 12:12 light dark cycle for induction of callus;
   c) excising the callus from the explant after a period of at least 40 days and subculturing the callus on fresh agar plates fortified with PES medium in the presence of cool white fluorescent lights with 40–60 μmol photon m$^{-2}$s$^{-1}$ irradiance and a 12:12 light and dark cycle to obtain differentiated densely pigmented oval or spherical shaped micro-propagules;
   d) subculturing blocks of the pigmented callus as an embedded culture in agar plates in Provasoli Enriched Seawater (PES) medium containing plant growth regulators, for a period of about 20 to 40 days, in the presence of cool white fluorescent lights of 20–60 μmol photon m$^{-2}$s$^{-1}$ irradiance and a 12:12 light and dark cycle to achieve profusely branched pigmented calli in each embedded block leading to enhanced somatic embryogenesis and micro-propagule formation in pigmented filamentous callus;
   e) transferring the filamentous calli with somatic embryos to liquid PES medium in an agitated condition for morphogenesis and development of young plantlets with multiple shoots from propagules; and
   f) cultivating algal biomass on a large scale in the sea by growing the young plantlets in enclosed perforated polythene bags.
2. A method as claimed in claim 1, wherein the material for tissue culture is a Rhodophytic marine alga selected from the group of genera of *Eucheuma, Gigartina*, and *Chondrus*.
3. A method as claimed in claim 1, wherein the material for tissue culture is an alga selected from the group of *Eucheuma striatum, Kappaphycus alvarezii, Eucheuma cottonii, Eucheuma denticulatum, Eucheuma spinosum, Eucheuma alvarezii, Eucheuma procrusteanum, Gigartina intermedia, Gigartina exasparata* and *Chondrus crispus*.
4. A method as claimed in claim 1 wherein the axenic explants comprise 1 to 6 mm long cuttings with 3–4 mm diameter and are selected from the upper or distal parts of the algae.
5. A method as claimed in claim 1 wherein the algal material is treated first with 0.1–1% domestic liquid detergent for 5 to 20 minutes, followed by treatment with 0.1–2% providine iodine for 2 to 7 minutes, and finally in provasoli enriched seawater with 1–5% antibiotic mixture for 04–96 hrs.
6. A method as claimed in claim 1 wherein the antibiotic mixture comprises penicillin, streptomycin sulphate, kanamycin, nystatin and neomycin in 100 ml distilled water.
7. A method as claimed in claim 1 wherein the axenic explants are cultured on agar plates containing 0.8–3% agar medium fortified with provasoli enriched seawater at 20–25° C. in the presence of cool white fluorescent light at 20–50 $\mu$mol photon $m^{-2}s^{-1}$ with a 12:12 light and dark cycle at 20–25° C.

8. A method as claimed in clam 1, wherein the calli of step 1(d) are subcultured by growing thin slices of pigmented calli as embedded cultures in agar plates containing 0.3–0.6% agar and made in provasoli enriched seawater medium at 20–25° C. in the presence of cool white fluorescent light at about 20–50 $\mu$mol photon $m^{-2}s^{-1}$ irradiance with 12:12 light and dark cycle to obtain profusely branched filamentous pigmented calli in each embedded block.

9. A method as claimed in claim 1 wherein the plant growth regulators are selected from 0.1–1.0 mg/l naphthalenacetic acid and 0.1 mg $1^{-1}$ each of naphthalenacetic acid and 6-benzylaminopurine.

10. A method as claimed in claim 1 wherein the axenic explants in step (b) are cultured on agar plates for a period of about 40–45 days.

11. A method as claimed in claim 1 wherein the algal biomass in step (f) are grown in 60×45 cm polythene bags attached to long floating lines in the sea and the crop is harvested after a period of about 60 days.

12. A method as claimed in claim 1 wherein the young plantlets at step (f) are cultured in perforated polythene bags with annual seawater temperature ranging from 22.5° C.–28.5° C., pH from 7.81–8.26, salinity from 24.0%–34%, dissolved oxygen from 7.84 ml/l–15.68 ml/l, phosphate from 0.02 $\mu$mol–3.23 $\mu$mol, nitrate from 0.15 $\mu$mol–2.58 $\mu$mol and nitrite from 0.01 $\mu$mol–0.85 $\mu$mol.

13. A method as claimed in claim 1 wherein the micropropagules in step (d) are clonally propagated through somatic embryogenesis of pigmented filamentous callus.

14. A method as claimed in claim 1 wherein the young plantlets in step (f) are grown in protective cultures in the sea for a period of at least 60 days in submerged transparent polyethylene bags with perforations, attached to floating long lines.

15. A method as claimed in claim 1, wherein said step of subculturing thin slices of the pigmented callus includes adding growth regulators including $\alpha$-naphthalene acetic acid and 6-benzylaminopurine to achieve further enhancement of formation of somatic embryos through somatic embryogenesis.

16. A method as claimed in claim 1, wherein a harvesting period after at least 60 days can yield a higher biomass of tissue cultured plant than that of a control of parent plants or wherein the biomass can be maintained constant and a cultivation period reduced from at least 60 days.

17. A method as claimed in claim 1, wherein a two fold increase in growth in fresh weight of tissue cultured plant is achieved over a control of parent plants, without change in carrageenan product yield and gel strength, through micropropagule formation from pigmented calli.

18. A method as claimed in claim 1, wherein the material for tissue culture is a Phaeophytic marine alga selected from the group of genera of *Luminaria, Undaria, Ecklonia, Eisenia, Macrocystis, Sargassum*, and *Turbinaria*.

* * * * *